(12) United States Patent
Wenger

(10) Patent No.: US 6,751,493 B2
(45) Date of Patent: Jun. 15, 2004

(54) UNIVERSAL ELECTROCARDIOGRAM SENSOR POSITIONING MASK WITH REPOSITIONABLE SENSORS AND METHOD FOR EMPLOYING SAME

(75) Inventor: William K. Wenger, Laguna Niguel, CA (US)

(73) Assignee: Unilead International, Inc., Lafayette, CA (US)

(*) Notice: Subject to any disclaimer, the term of this patent is extended or adjusted under 35 U.S.C. 154(b) by 329 days.

(21) Appl. No.: 10/044,530

(22) Filed: Jan. 9, 2002

(65) Prior Publication Data
US 2003/0130585 A1 Jul. 10, 2003

(51) Int. Cl.$^7$ .............................................. A61B 5/0408
(52) U.S. Cl. ........................ 600/382; 600/509; 600/391; 600/393
(58) Field of Search ................. 600/382, 386, 600/388–393, 509

(56) References Cited

U.S. PATENT DOCUMENTS

| | | | | |
|---|---|---|---|---|
| 4,498,480 A | * | 2/1985 | Mortensen | 600/393 |
| 4,583,549 A | * | 4/1986 | Manoli | 600/393 |
| 5,327,888 A | * | 7/1994 | Imran | 600/393 |
| 5,465,727 A | * | 11/1995 | Reinhold, Jr. | 600/390 |
| 5,507,290 A | * | 4/1996 | Kelly et al. | 600/393 |
| 5,678,545 A | * | 10/1997 | Stratbucker | 600/382 |
| 5,782,238 A | * | 7/1998 | Beitler | 600/388 |
| 5,788,633 A | * | 8/1998 | Mahoney | 600/382 |
| 5,868,671 A | * | 2/1999 | Mahoney | 600/382 |
| 5,995,861 A | * | 11/1999 | Price | 600/372 |
| 6,006,125 A | | 12/1999 | Kelly | 600/382 |
| 6,115,623 A | * | 9/2000 | McFee | 600/372 |
| 6,553,246 B1 | * | 4/2003 | Wenger | 600/382 |

* cited by examiner

*Primary Examiner*—Carl Layno
(74) *Attorney, Agent, or Firm*—Bruce & McCoy; Ernest H. McCoy

(57) ABSTRACT

A universal disposable ECG sensor positioning device and method for use with electrocardiogram diagnostic equipment in which the mask has six sensors, two of which are movable, to provide four different sizes to accommodate varying sized human torsos.

10 Claims, 2 Drawing Sheets

UNIVERSAL ELECTROCARDIOGRAM SENSOR POSITIONING MASK WITH REPOSITIONABLE SENSORS AND METHOD FOR EMPLOYING SAME

RELATED APPLICATIONS

This is a related application to U.S. patent application Ser. No. 09/461,701, filed Dec. 14, 1999, now U.S. Pat. No. 6,400,977, for A Universal Electrocardiogram Sensor Positioning Device and Method, which is a continuation of U.S. Pat. No. 6,006,125, issued Dec. 21, 1999.

BACKGROUND OF THE INVENTION

1. Field of the Invention

The present invention relates to a disposable dermal chest mask for assistance in establishing electrical communication between sensors on a human chest and electrocardiograph machines. More particularly, it relates to a universal electrocardiogram sensor positioning device and method for all adult sizes including size extra large.

2. Description of the Prior Art

Diagnostic medical equipment increasingly relies upon electrical contact with specific areas of the human body for evaluating the health status of patients. One of the most utilized and relied upon diagnostic tools is the electrocardiogram, sometimes referred to as an ECG. Leads or signal wires from the analytical apparatus are attached to a metallic or otherwise conductive body sensor electrode which is attached to the patient's skin at the desired points of contact. Electrical current generated by the heart in a person's chest flows to the surface and at the skin produces differences in electrical voltage which can be measured between pairs of electrodes placed at two points on the skin. A twelve-lead electrocardiograph provides the most accurate signals for recognizing ischemic electrocardiographic changes.

To administer a resting twelve-lead ECG, it is necessary to apply ten electrodes to various points on the torso and limbs of a patient to measure and analyze cardiac data. Twelve recordings for the ECG are made from nine active lead positions with the tenth being used as a ground. An electrode portion of a lead may in fact consist of an alternative form of sensor, and the terms "electrode" or "sensor" for purposes of this disclosure are interchangeable. A lead wire connecting a sensor to the diagnostic equipment could possibly in fact consist of a radio or an optical signal. Six of the ten electrodes are applied to the patient's chest over prescribed anatomical landmarks. The remaining four electrodes are applied to each of the patient's limbs. The chest electrodes are known as the precordial leads and the limb electrodes are called limb leads. The precordial leads are designated $V_1$, $V_2$, $V_3$, $V_4$, $V_5$, and $V_6$. The limb leads are designated LA, RA, LL, and RL (ground).

It is generally acknowledged that it is critically important to place the precordial leads with precision in order to obtain accurate and repeatable recordings. However, accurate placement and attachment of a large number of leads can be difficult and time consuming and requires knowledge, skill, and diligence on the part of the person attaching the electrodes or sensors. Mechanical problems in attaching multiple leads to a patient range from tangling of lead wires, and excessive time consumed in pairing lead wires with the appropriate electrodes, to difficulty in locating anatomical landmarks on a patient with precision.

Problems occur if the leads are not properly placed and are located higher or lower than optimal. The position of the precordial leads is determined by the anatomical features of the patient's chest and not by the position of the heart itself. Research reported in the electrocardiography literature indicates that precordial leads placed one inch or more from their true anatomical landmarks can result in misinterpretation of the patient's ECG. This may result in or contribute to diagnosis errors, false hospital admissions, sending sick people home, or have other negative impacts on diagnosis or treatment. The placement problem is compounded when serial comparisons are made between two or more ECGs taken over time. For example, if $V_4$ was placed one inch too high for one test and one inch too low for another, the difference of two inches may produce what appears to be a significant difference between the two ECGs when in fact there was no physiological change in the patient's heart condition.

To place the precordial leads accurately requires training in using both visual and palpatory cues to find the anatomical landmarks on each patient. Placement accuracy is also affected by the time and diligence dedicated to placing the precordial electrodes. An experienced and conscientious electrocardiologist may require and devote ten minutes to palpation and ascertaining the exact precordial landmarks. However, in busy clinical environments or emergency situations, medical personnel are often so rushed they may not even palpate the patient. Under those conditions, precordial leads are commonly placed with inadequate palpation and with little attention to a patient's particular anatomy. As a consequence, individual leads are often misplaced by two and as much as three inches from their true anatomical landmarks. In addition, training and maintaining the necessary skill for proper placement of individual leads is time and resource consuming and often not adequate. With six precordial leads, there are six chances to misplace electrodes. Research shows that $V_1$ and $V_2$ electrodes are typically placed high and wide of their targets—the fourth intercostal space on each side of the sternum. Likewise, precordial electrodes $V_4$, $V_5$, and $V_6$ are most often misplaced low and wide. Electrode $V_3$ is most often misplaced too low. The most obvious conclusion to be drawn is that lead placement is often not accurate.

After the individual electrodes are positioned on a patient, it is necessary to attach the ten lead wires. Each lead wire is labeled to correspond to one of the anatomical landmarks, i.e., $V_1$, $V_2$ ... $V_6$ ... RL. Should lead wires be crossed, interpretative ECG monitors can detect and alert the operator of a possible crossed lead wire situation, but that requires additional time to check connections and to take corrective action. This is a time consuming operation which increases the risk in an emergency situation. Crossed lead wires are a more significant problem when the ECG monitor does not provide interpretation of the recordings and cannot alert the operator of this possibility. In such a case, the ECG signals for each of the twelve leads are recorded on hard copy to be read at a later time. The physician or technician reading the ECG recordings may recognize the error but by that time the patient has usually been disconnected from the monitor. The present invention reduces or eliminates the chances of either of these situations from occurring.

Periodic electrocardiograms are important for providing a cardiographic profile of a patient for early detection and diagnosis of cardiovascular diseases. In order to provide an accurate profile, it is important not only that the electrocardiogram be taken with sensors affixed accurately, but that the sensors be placed at the same location on the patient in the subsequent exam as for the previous examination. The efficacy and the repeatability of the tests is critical so that a series of ECG results can be compared to provide a continuing profile of a patient's medical history for diagnosis and treatment of heart disease.

In urgent situations, including those electrocardiograms taken with the current standard electrode lead wire system, during an acute symptomatic episode there may only be time to attach two to four individual electrodes to the patient. Therefore, it is desirable to have a device which enables more electrodes or sensors to be quickly and accurately secured during such an acute symptomatic episode. Alternatively, it may be necessary to quickly remove some or all of the chest leads when a patient is experiencing a heart attack or in other emergencies in order to administer CPR, to massage the heart, administer drugs, to apply electrical defibrillation paddles, or for other purposes. Accordingly, critical time can be lost both in the removal of the chest leads of the ECG test equipment in order to administer aid to a patient and in their subsequent replacement after aid has been administered.

Because of the inadequacies of prior art devices to solve these problems, there has been a need for a system which: prevents or curtails the possibility of ECG electrode leads or wires from being entangled or crossed; provides quick removal of some of the sensors when it is necessary to administer aid to a patient having a heart attack; provides accurate and appropriate repeatable placement of electrodes at substantially the same location on the patient; accurately and repeatedly obtains signals from electrodes by efficient and effective electrical transmission; and may be attached by persons with varying levels of experience including those with little training.

The inventions disclosed in the five related patents to Kelly—U.S. Pat. No. 5,865,740, No. 5,865,741, No. 5,916, 159, No. 6,066,093, and No. 6,157,851—involve various alternatives for the purpose of trying to effect those goals. The common invention in those patents is a disposable electrode positioning device and utilizes a non-conducting flexible sheet in the form of a mask having a predetermined dimensional sensor array. The flexible sheet serves as a template for aligning connectors or sensors, either of the electrode or electrodeless type, on the chest of a patient for transmitting electrical impulses.

An important aspect of the Kelly inventions is that the flexible non-conductive sheet is provided in a plurality of sizes, with each size having arrays $V_1$, $V_2$, $V_3$ and $V_4$, at substantially the same locations and having arrays $V_5$ and $V_6$ at different locations depending on size. In this regard, the locations of $V_5$ and $V_6$ are based on a measured distance between the left midclavicular line and the left midaxillary line on the chest of a patient.

An alternative of the related inventions is that the dimensional array on the flexible non-conductive sheet is provided with cutouts to form a template or mask which is placed on the patient's chest and then conventional electrodes can be positioned in the cutouts. Still another aspect of the related inventions is that the template can be provided with a plurality of conventional tab, snap, or other electrodes affixed on their top sides to the flexible sheet to be placed against the patient's chest. The electrodes are positioned in accordance with the predetermined dimensional array. Small cutouts, or openings, in the template expose the electrode tabs for attaching lead wire clips. Snap electrodes protrude through the template to permit the attachment of lead wire snap connectors.

In a further aspect of the related inventions, the top sides of individual electrodes can be lightly affixed to the flexible sheet of material at the predetermined dimensional array locations. The sheet can be placed on the patient's chest and then peeled away leaving the electrodes properly located on the chest. Each of these concepts can be employed in the concept of the basic embodiment of the present invention as disclosed in the related patent application and U.S. Pat. No. 6,006,125 described earlier.

Yet another aspect of the Kelly inventions is a method of sizing a patient for fitting a sensor positioning device having a flexible sheet with a fixed dimensional $V_1$–$V_6$ array positioned in a specific size configuration appropriate for standard electrocardiographic recording. The distance between $V_1$ and $V_2$ is a predetermined distance plus or minus a small amount, and the distance between $V_2$ and $V_4$ is a predetermined distance plus or minus a small amount, with $V_3$ located substantially midway between $V_2$ and $V_4$, and $V_5$ being equidistant between $V_4$ and $V_6$. The method of sizing the disclosed related inventions comprises the steps of measuring the distance between the midclavicular line and a midaxillary line on the chest of the patient, and selecting a positioning device size of those inventions based on the measured distance. This procedure is eliminated by the related application, the '125 patent, and the present invention.

The prior art U.S. Pat. No. 4,583,549 to Manoli and the U.S. Patents to Kelly describe precordial electrodes fixed in a preset pattern on a flexible sheet in positions corresponding to the anatomical landmarks on the patient. The basic problem with all of these inventions is that they require multiple sizes of sensor positioning devices to fit various sized persons.

Manoli envisions, without stating any dimensions, three sizes—a pediatric, medium adult, and large adult—to fit most children and adults within the population. Kelly describes three sizes—small, medium, and large adult—to fit most adults within the population. Manoli does not describe how one determines which size device a patient would require. Presumably, under Manoli, a small person requires the smallest of the three sizes, i.e., the pediatric, and a large person requires the largest. The invention disclosure is indefinite in this regard.

Thus, Manoli does not describe how to size a patient, and it is common for persons placing individual electrodes to make errors. If similar errors are made when sizing the patient for Manoli's device, it is quite likely that the wrong size device would be selected. Once a device is applied to the patient, it would be possible to check the correctness of fit. If wrong, however, i.e., the $V_6$ electrode was located some distance from the patient's midaxillary line, the device would have to be removed and replaced by a more appropriate size device. This trial and error approach wastes time and materials since the first device would need to be discarded without ever being used to take an ECG.

The more recent U.S. Pat. No. 5,678,545 to Stratbucker describes an adhesive sheet having a fixed array of individual electrode groups disposed at varying locations to provide a "one size fits all" system. One embodiment has twelve precordial electrodes with one electrode each at $V_1$, $V_2$, and $V_3$ and groups of three electrodes each at $V_4$, $V_5$, and $V_6$, while other embodiments are suggested for groups of electrodes for other electrode locations in order to achieve a "one size fits all" system.

Stratbucker describes multiple groupings of electrodes for a "single size" system but it is necessary to determine which electrode in each group is within the region of the appropriate location on a patient's chest: for each group of electrodes, there must be a determination of which electrode is closest to the anatomical landmark. Such a determination is time consuming and would at least be impeded by the fact that palpation will be difficult to perform once the sheet is placed over a patient's chest. Moreover, each group of electrodes provides a source for error since there are three electrodes to choose from in each group. Assuming one electrode in each group is most correct, the probability of randomly selecting the best electrode from each of the groups is $0.33^X$, where X equals the number of groups. If there are three groups of electrodes, as described in one embodiment where $V_4$, $V_5$, and $V_6$ consist of groups of three electrodes each, the probability of randomly selecting the appropriate electrode from each group is 0.037, or 1 out of 27 possibilities. Stratbucker relies on a judgment determination for each group of electrodes and therefore selection is time consuming and inexact due to the device physically covering the patient's anatomical features.

Although Stratbucker tries to curtail the possibility of placing conventional individual electrodes far from the region of proper placement by confining the decision to simply selecting one electrode out of each group of three electrodes, medical personnel must still ascertain which electrode is appropriate for each group of electrodes. Not only does this allow for error, it also reduces the chances of consistent electrode placement from one test to the next, thereby confounding any serial comparisons between tests. It also increases the length of time to administer a resting ECG since a separate decision must be made for each group of electrodes.

The related invention of U.S. Pat. No. 6,006,125 uniquely solved those problems by providing a multiple precordial array of sensor electrodes in a single device that will fit essentially three classes of sizes of adults and in which sizing is accomplished simply by the determination of the location of a single sensor which is closest to a selected anatomical landmark. This is achieved by a device having more precordial sensors than the six chest electrodes needed for the resting ECG but significantly less than the number of those taught by Stratbucker.

In the '125 invention, some sensors may serve multiple roles to accommodate different patient sizes within one array by utilizing a particular set of sensors. Each set of sensors corresponds to a specific patient size that can be characterized as small, medium, or large. Once the device of the invention is applied to the patient, one simply and quickly ascertains which of three $V_6$ sensors lies on or closest to the patient's midaxillary line and then connects the electrode sensor lead wires to the corresponding set of sensors in which the $V_6$ is designated as one of the three selections: small, medium, or large. The invention of the '125 patent greatly simplifies the heretofore universal unresolved problem of instantaneous patient sizing during use, while providing the additional benefits of reducing the cost of production and eliminating the need to stock different size devices.

The present invention differs from prior art parent U.S. Pat. No. 6,006,125 described in the related applications portion of this specification to provide several advantages. The '125 patent covers three classes of human torso sizes which, by accurate estimate, includes ninety percent (90%) of the adult population and a substantial portion of the teenage population. The ten percent (10%) of the adult population not covered are the extra-large persons of which there is a substantial representation in the human population. The present invention provides a unique modification to the '125 patent which accommodates nearly all of the extra-large size torsos whereby the present invention will fit all of the adult population as well as a substantial portion of the teenage population.

The invention's co-pending application for A Universal Electrocardiogram Sensor Positioning Device and Method for Four Sizes Including Extra Large, Ser. No. 10/021,937, filed Dec. 13, 2001, addresses this problem but does not completely solve it. The present invention allows for exploratory placement of the $V_5$ and $V_6$ sensors for the reason that the sensors are detachable from the mask, allowing traces to be taken at sensor sites adjacent to a patient's normal sensor sites.

There is also a savings in the cost of manufacture of the present invention for the reason that the number of relatively expensive leads and sensors that are electrolessly deposited or imprinted onto the mask during manufacture are substantially reduced. Likewise, the specialized electrical clip utilized for attaching the ECG machine to the mask is greatly simplified and, in fact, one does not even need to be utilized as the leads from the machine can be attached directly to the mask or by the use of a standard multi-connection electrical clip.

SUMMARY OF THE INVENTION

The present invention is a universal ECG multiple sensor dermal precordial mask for fitting different sizes of human bodies including extra large for obtaining electrocardiographic information using sensors $V_1$, $V_2$, $V_3$, $V_4$, $V_5$, and $V_6$. The mask is comprised of a sheet of non-conductive material incorporating at least six sensors and ten sensor positions disposed in a specific geometric arrangement with the $V_1$–$V_4$ sensors being utilized for all sizes of bodies. The ten sensor positions include four alternate positions for each of the $V_5$ and $V_6$ positions. The $V_5$ and $V_6$ sensors have first and second independent sensor positions each and first and second shared positions. The $V_5$ and $V_6$ sensors are releasably secured to the sheet and detachable, repositionable, and resecurable to any of the four separate sensor positions for each of $V_5$ and $V_6$.

The present invention also includes a method for obtaining electrocardiograms by means of a universal ECG multiple sensor dermal precordial mask incorporating sensors $V_1$, $V_2$, $V_3$, $V_4$, $V_5$, and $V_6$ for fitting different sizes of human bodies including extra large. The steps of the method include providing a mask which has at least ten precordial sensor positions disposed in a specific geometric arrangement forming at least four sets of sensor groups which include four alternate sensor positions for each of the $V_5$ and $V_6$ sensors. Four sensors are disposed in the $V_1$–$V_4$ sensor positions and are utilized for all sizes of bodies. The $V_5$ and $V_6$ positions each have two independent sensor positions and share two positions corresponding to the four sensor sets. The $V_5$ and $V_6$ sensors are releasably secured to the mask and can be detached therefrom with similarly detachable variable length and flexible leads formed integral thereto whereby the $V_5$ and $V_6$ sensors are repositionable to each of the respective $V_5$ and $V_6$ alternate positions.

The mask includes indicia for determining which alternate $V_5$ and $V_6$ sensor positions. A pair of repositionable sensors and leads is provided and corresponds to the four sensor sets. The mask is aligned on a patient's chest so that the $V_1$ and $V_2$ sensors are disposed approximately on opposite sides of the patient's sternum so that it may be ascertained from the indicia which of the four $V_6$ sensor positions lies on or is closest to the patient's midaxillary line. If necessary, the releasably secured sensors may be detached and repositioned to the corresponding set of sensor positions having $V_6$ lying closest to the patient's midaxillary line. Electrocardiographic information is obtained from the fixed $V_1$–$V_4$ sensors and the movable $V_5$ and $V_6$ sensors.

OBJECTS OF THE INVENTION

It is therefore an important object of the present invention to provide an ECG multiple sensor positioning device which is universal whereby one size fits all including extra large rather than requiring a multitude of different sizes thereby achieving economic benefits of high volume production and simplified sales and distribution.

It is another object of the present invention to provide a universal ECG sensor mask and method of use in which less time is needed to perform an ECG since the steps used to determine which mask size to utilize are eliminated.

It is a further object of the present invention to provide a disposable universal ECG sensor positioning device which can be thrown away after use providing less risk of transmitting infection and one in which the logistics of maintaining different size devices in inventory are eliminated.

It is still another object of the present invention to provide a universal ECG sensor mask and method of use in which, simplified, efficacious, and repeatable sensor placement results are guaranteed.

It is yet a further object of the present invention to provide a multiple sensor mask and method of use in which a twelve-lead electrocardiogram, which provides the most comprehensive recordings of electrical activity of the heart for recognizing ischemic electrocardiographic changes, can be obtained quickly and repeatably from a single size mask.

It is still another object of the present invention to provide a universal ECG electrode mask and method of use in which four different ECGs can be performed by the same device.

And it is still a further object of the present invention to provide a universal electrocardiogram sensor mask which covers essentially all (100%) of the adult human torso population including extra large sizes and a large portion of the teenage population.

Other objects and advantages of the present invention will become apparent when the method and apparatus of the present invention are considered in conjunction with the accompanying drawings.

DESCRIPTION OF THE PREFERRED EMBODIMENT

Reference is made to the drawings for a description of the preferred embodiment of the present invention wherein like reference numbers represent like elements on corresponding views.

Figure 1:
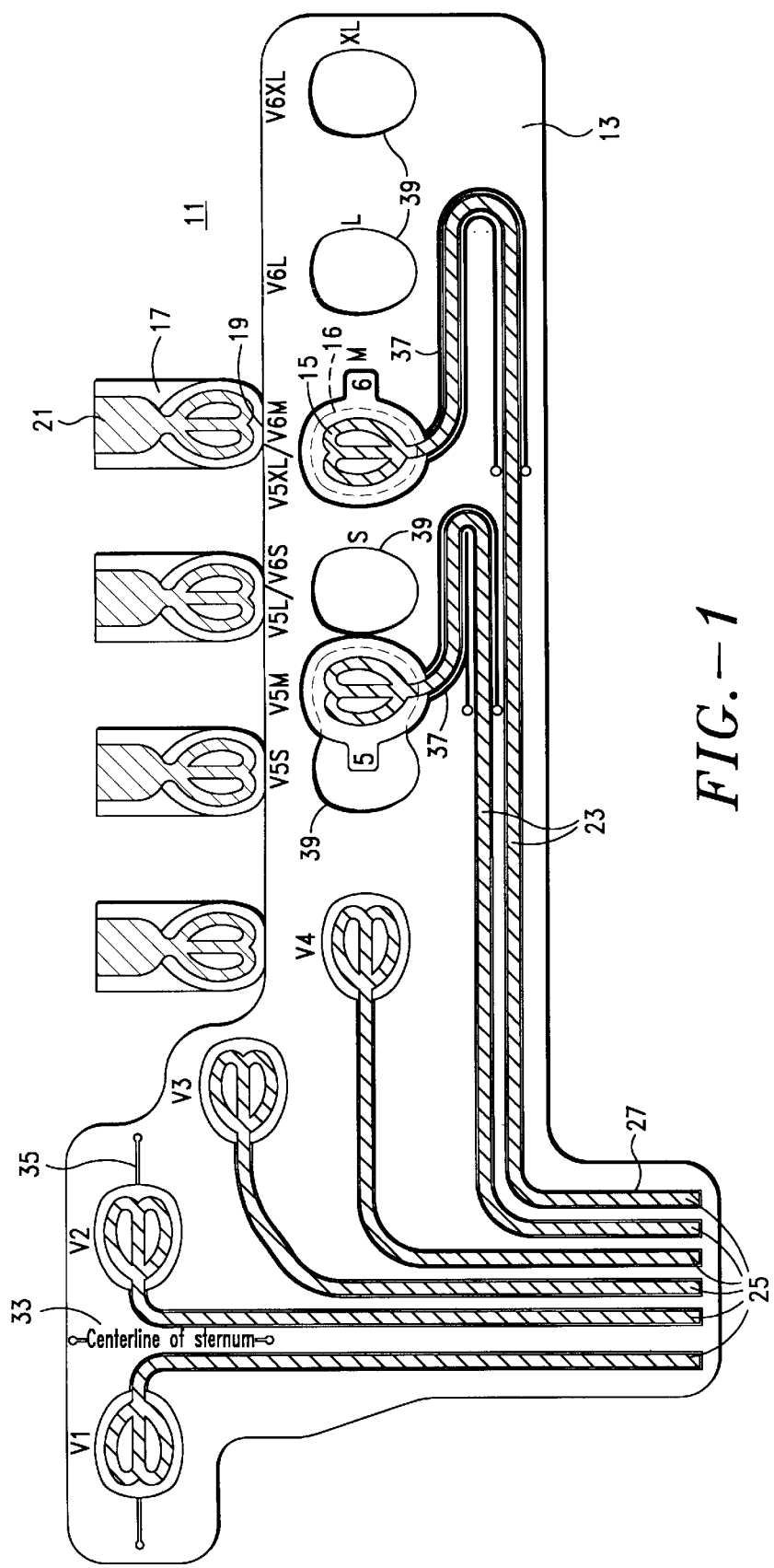
FIG. 1 is a plan view of the Universal ECG Sensor Positioning Device of the present invention.
Figure 2:
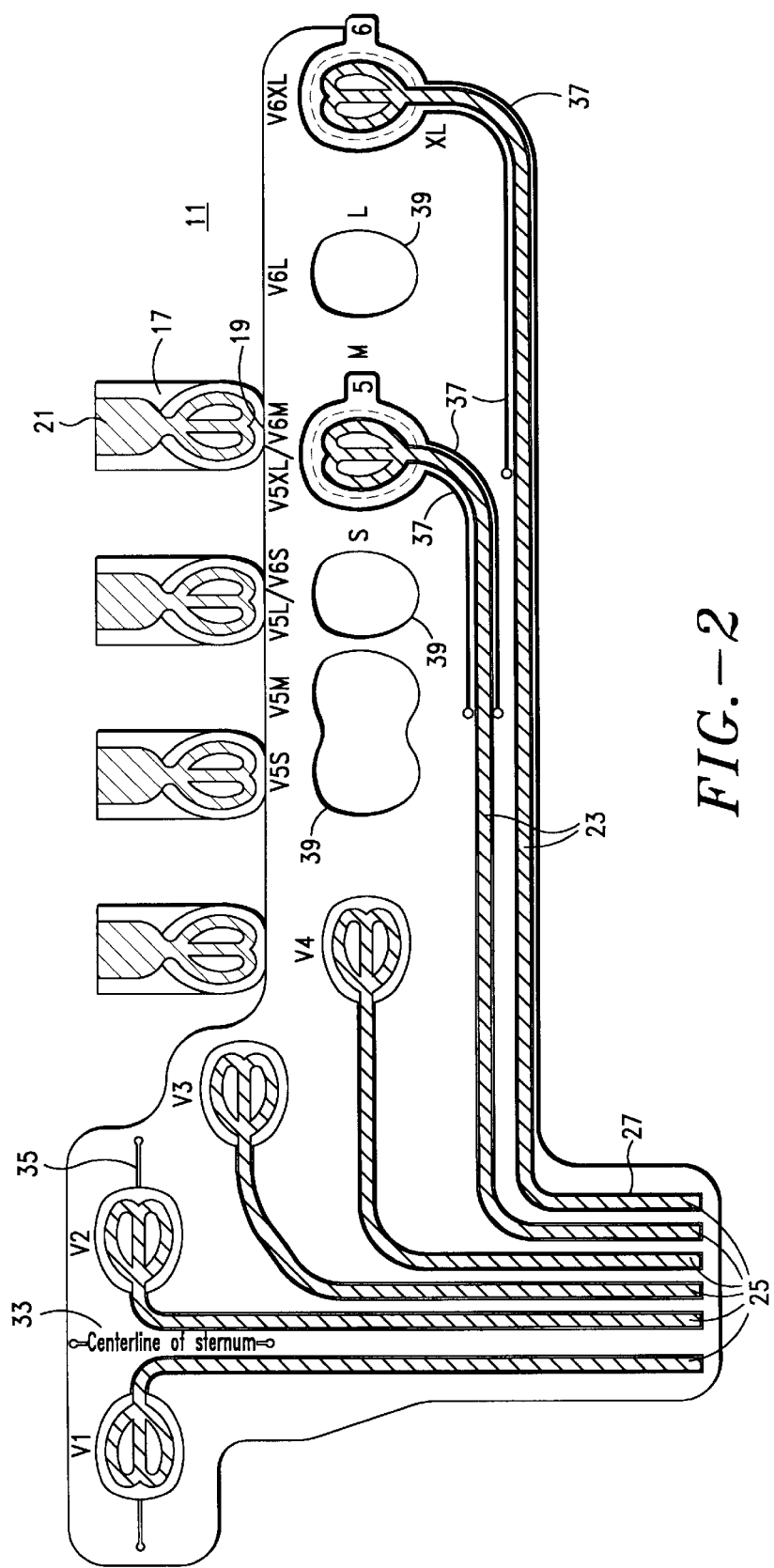
FIG. 2 is an alternative embodiment thereof

FIGS. 1 and 2 illustrate alternative plan views of the universal disposable ECG sensor positioning device of the present invention for placement on the chest of a patient for performing an ECG test. The word "universal" as used in describing the device is an abbreviation of the descriptive colloquial terminology—one size fits all. The devices of the related inventions fit ninety percent (90%) or more of the adult population and most older children as well, while the present invention fits essentially all of the adult population.

However, overweight and extra large torso persons have a disproportionately larger number of heart related problems than the general population. It is therefore important to provide a universal ECG sensor positioning device which can be utilized for this portion of the population as well as the general adult population. It has been determined that this can be done by a novel modification and improvement of the related inventions. It is believed that the device of the present invention can be used to fit essentially all of the adult population because it permits a wider selection of $V_5$ and $V_6$ sensor placement on very large persons.

The term "disposable" means that the device is intended for a single or one time use only. However, the physical form of the device could be reusable for more than one test, and a more permanent embodiment of the design could be a truly reusable device possibly requiring sterilization, cleaning, and/or fresh adhesive for reuse. Therefore, the term "disposable," as used in the descriptive preamble of the claims, is provided solely as an aid for most accurately describing the preferred embodiment of the invention in relation to the prior art and should not be interpreted as a limitation on the forms of the invention and scope of the claims.

The device is a dermal chest mask 11 which is formed of a sheet of flexible non-conducting material 13 for carrying or positioning six chest electrodes or electrodeless sensors 15 which will accommodate four different classes of human torsos. The sensors are connected by electrical lead wires integral to the mask and to a standard electrocardiographic diagnostic machine through an electrical connection between the mask. The alternate means for sensor placement is designated in the claims hereof by the term "sensor positions" which includes all of the aforementioned means for sensor placement.

The flexible non-conductive web or sheet may be formed from any preferably transparent natural or synthetic material which is capable of accepting a print. Generally any cellulosic material, polyester, polyolefin, polyvinyl chloride, nylon or mixtures thereof would be suitable. Cotton, polypropylene, or polyethylene can be used if cost is a consideration. However, polyester is likely the most preferable.

The form of the invention incorporates the ECG sensors 15 into the flexible sheet 13. Two of the sensors are movable by being releasably secured to the mask with detachable variable length and flexible leads formed integral thereto. The detachable sensors and their leads can be repositioned at designated sensor positions, such as holes formed in the mask, in a specific geometric pattern called for herein on the flexible sheet. The sensors can be adhered to the patient's skin through the holes or to the membrane of the mask if it is electrically conductive in the alternate areas of the sensor placement.

Detachable limb lead sensors 17 can also easily be provided integral to the mask during the manufacturing process. In a preferred embodiment, they are formed as appendages secured to the mask with a means for easy detachment such as a set of perforations along the line of joinder 19 of the limb lead sensor to the mask 11. The ends of the limb lead sensors are provided with an electrical contact area 21 whereby an electrical lead can be connected to the sensor by any appropriate means such as an electrical connector clip.

The receptor sensor electrode positions 15, which are located on the mask 11, are spaced relative to each other in a specific geometric configuration appropriate for electrocardial recordings from all sizes of adult human torsos. Each receptor sensor or electrode position is adapted for electrical connection with the skin of a patient's body for detecting and transmitting electrical signals generated by the patient.

The mask includes conductor strips 23 each of which extends to and electrically connects to a sensor. The other end of each conductor strip terminates in a connector end or terminal which engages any type of connection or cable junction for electrical connection with the electrocardiograph analyzer. Six discrete electrical contacts are provided in an aligned array for connection to an ECG machine to accommodate all four different classes of adult human torso sizes. The six individual terminals 25 for $V_1$ to $V_6$ are contiguous, and the terminal ends of the strips are preferably disposed aligned with each other to facilitate connection to a common connector which can be utilized for all four classes of sizes. A standard clip is envisioned to simplify use of the mask of the present invention by permitting a single-clip connection.

The sensors and leads are formed integral to the mask and means are required to enable the sensors. In order to establish electrical connection between a human body and the receptor sensor positions 15, a biocompatible electrically conductive adhesive, such as hydrogel, is applied to the body contacting side of the sheet at each sensor for adhesion to the skin of the patient. It is generally transparent and shown in outline 16 in the drawings. Hydrogel is commercially available as are other suitable conductive adhesives and any suitable electrodermal adhesive would serve the purpose. The size of the adhesive area is generally between 3 and 9 square centimeters. When the mask is pressed against the skin of the patient's chest, the sensors are electrically connected to the patient at each receptor.

The gel-coated adhesive area of the mask 11 includes at least one release liner in releasable adhesive contact with the gel covering the sensors 15. Because the release liner can be transparent, and is simply a sheet of material, it is not shown in the drawings. Separate release liners could be provided for each sensor, but in the preferred embodiment, a single release liner covers all of the sensors and the liner can be removed from the mask in a single operation to expose all of the sensors as a unit. An exception may be the limb lead sensors and possibly the two movable sensors. The limb lead sensors 17 are released individually having been separated at the perforations 19 along the line of joinder with the mask, and the moveable sensors may or may not be moved depending upon the size of the patient.

The flexible release liner covering the receptors may be made from a suitable dielectric film or coated paper which includes polypropylenes, polyesters, olefinic polymers, polyvinyl chloride and its copolymers, acrylic rubbers, ABS resin, and the like. Commercial suppliers for these materials are listed in the related applications.

The receptor electrodes 15 and the conductor strips 23 can be produced from any electrically conductive material, e.g., metal, foils, conductive polymers, graphite, carbon fibers, and the like. They include gold, copper, silver, tin, aluminum, N-vinyl pyrrolidone, and alloys or mixtures thereof. The receptor/conductors can also be made from a conductive paste of a metal in particle form in a suitable binder which is printed or silk screened onto the flexible non-conductive sheet or electrolessly deposited. A connective polymer may be heat pressed or otherwise conventionally secured to the web or sheet.

Copper strips could be utilized and electrolessly deposited on the polymeric sheets in a range of thickness from about 0.25 to about 5 microns, more preferably from 0.25 to 1.5 microns, and most preferably 0.4 microns in thickness. A metallic ink may be preferable such as a commercially available silver ink. Each of the conductor strips are less than 10, and preferably less than 5, micrometers in thickness, whereby the flexibility of the connector and adhesion of the gel surface to the skin are substantially enhanced.

The exposed conductive strips 23 may be partially covered with a dielectric layer for insulating the conductive pathways. This coating can be transparent and is also shown in the drawings in outline 24. The strips are coated with a dielectric polymeric material in such a way so that only selective portions comprising the sensor 15 and the electrical contact or terminal areas 25, 27 are exposed. Suitable dielectric coatings include polyesters, ethylene-vinyl acetate copolymers, polyvinyl chloride and its copolymers, terpolymers such as acrylonitrile-butadiene styrene (ABS resins) and inter alia.

Therefore, a preferred laminate for the flexible sheet of the invention can comprise several layers, several of which can be transparent. A preferred embodiment of the invention would include: (1) a base layer of a flexible non-conductive film of polyethylene terphthalate; (2) a bond layer for the conductor strips such as a catalyst in contact with a conductive ink; (3) a conductor strip comprised of silver ink; (4) an adhesive layer such as hydrogel superimposed upon the silver ink in the sensor areas of the mask, or alternatively, a dielectric layer superimposed upon the silver ink in the conductor strip area of the mask; and (5) a flexible release liner as the top layer superimposed upon at least the adhesive layer of the mask.

Since the device of the present invention is designed for use by untrained personnel as well as a trained individual, the sheet material of the mask contains designator markings or indicia to simplify attaching to or positioning of the mask on the patient's chest. It is sufficiently self-describing such that it allows a person untrained in electrocardiography to position the mask to obtain highly reliable and repeatable ECG signals. It also includes indicia for sizing the patient.

FIGS. 1 and 2 show the six-sensor ten position array which includes singular $V_1$, $V_2$, $V_3$, and $V_4$ sensor positions and four alternate $V_5$ and $V_6$ sensor positions each. The $V_5$ and $V_6$ positions each have two independent sensor positions ($V_{5S}$, $V_{5M}$, $V_{6L}$, and $V_{6XL}$) and share two positions ($V_{5L}/V_{6S}$ and $V_{5XL}/V_{6M}$). The FIGS. also show the indicia therefor. Indicia V1, V2, V3, and V4 indicate a single position for each of the $V_1$, $V_2$, $V_3$, and $V_4$ sensors. Indicia V5S indicates $V_5$ small; V5M indicates $V_5$ medium, V5L/V6S indicates either $V_5$ large or $V_6$ small. V5XL/V6M indicates either $V_5$ extra large or $V_6$ medium. V6L and V6XL correlate to $V_6$ large and extra large, respectively. The additional indicia between V1 and V2, and V6M and V6L, aid the user in positioning the mask.

The ten sensor positions 15 are disposed on the flexible sheet 13 which is designed to adhere to a human torso so that the receptor sensors are located upon the precordial area of the chest and above the epigastric region of the abdomen. Six sensor positions indicated by the indicia V5S, V5M, V5L/V6S, V5XL/V6M, V6L, and V6XL are arranged in a precordial sensor array which can be rearranged to provide four sets of six sensor positions each. Two of the sensors serve as different designated sensors in the four different sets.

The six precordial sensors are disposed in a specific universal geometric arrangement rather than in predetermined fixed arrays of individual classes of sizes of sensor groups, as taught in the related cases and the Kelly and Manoli patents, or in multiple all-inclusive sensor group arrays as taught by the Stratbucker '545 singular patent. Nor are they positionable in an arbitrary individually located array of six precordial sensors as would be placed by a technician for a resting ECG.

In the present invention, four sensors, $V_1$–$V_4$, are fixed in position and two sensors are movable to form four sets of sensor groups, including four positions for each of the $V_5$ and $V_6$ positions, in which two sensor positions serve for either $V_5$ or $V_6$ in four different sensor sets. As a result, four sets of six sensors each are provided by the four fixed and two movable sensors to position them proximate to the anatomical landmarks of four different classes of human torso sizes including extra large.

The flexible sheet 13 can be essentially transparent and also includes self-explanatory first and second sets of indicia 33, 35 for aligning the mask on both the centerline of the patient's sternum and on the fourth intercostal space, respectively, whereby at least four sets of sensor positions on the mask, comprising six sensors each, accommodate four different classes of human torso sizes. In addition to facilitating correct placement of the receptors on the precordial areas of the human torso, the indicia also provide for selecting the correct set of sensor positions for the torso size and show which sensors are to be used. The precordial indicia indicate which sensor positions correlate to which torso size and that two of the sensor positions are shared or utilized for four classes of torso sizes but numbered as different designation sensor positions, $V_5$ or $V_6$. The indicia also provide for determining which alternate $V_5$ or $V_6$ sensor positions correspond to the four sensor sets for the movable sensors. Indicia 29 for the electrical connections to the ECG machine are also essentially self-explanatory.

When the electrodermal connectors are properly positioned for attachment to a patient, the position of the receptors at $V_1$ and $V_2$ are disposed to lie approximately on opposite sides of the patient's sternum at the fourth intercostal space as shown by the indicia 33, 35. The receptors at $V_3$ and $V_4$ are attached over the ribs, with $V_3$ positioned approximately equidistant between $V_2$ and $V_4$, and with $V_4$ positioned approximately over the intersect of the fifth intercostal space and the left midclavicular line. The receptors at $V_5$ and $V_6$ are placed at the side of the torso so that $V_5$ is substantially midway between $V_4$ and $V_6$.

In positioning the array of receptors for the preferred embodiment of the present invention, it has been found that the distance between $V_1$, $V_2$, $V_3$, and $V_4$ can be consistent for all sizes of human torsos. The dimensions between $V_1$, $V_2$, $V_3$, and $V_4$ have been developed to accommodate nearly all adults within tolerances acceptable for the resting ECG. It has also been found that body placement for receptors $V_5$ and $V_6$ vary depending on individual size. These variations are uniquely accommodated in one size mask by the present invention.

There is a novel method provided by the present invention for determining the proper size selection of electrode sets, i.e., for selecting six of the ten sensor positions for performing an ECG depending upon the torso size of the patient. The selection of the six sensors is ascertained by determining which one of the same designation sensor positions in each set lies closest to a selected precordial landmark whereby the set containing that closest lying position is selected as the set of six sensors to be utilized. As with $V_1$–$V_4$, it has been determined that the distance from the $V_4$ sensor position to the $V_6$ sensor position determines the size of a patient. For the inventions disclosed in the prior related applications, the measurement of this distance is determined by having the applying technician measure, such as by using his/her thumb and the middle finger, the distance between the midclavicular line and the midaxillary line on the chest of the patient. This distance is then compared to a sizing scale to select the proper size of device. The present invention, however, does not require any type of intermediate step to determine a patient's size. Rather, the device is applied to the patient and a simple visual observation ascertains which of four $V_6$ sensor positions lies closest to the patient's midaxillary line to establish that patient's size and the selection of the corresponding sensor set.

The distance between $V_4$ to $V_6$, that is, the distance between the midclavicular line and the midaxillary line on the patient, varies within predetermined limits based on the size of the torso. For a small size, the distance between $V_4$ and $V_6$ can range from about 2.5 to 4.5 inches; for the medium size, the distance can range from about 4.0 to 6.0 inches; for the large size, the distance can range from about 6.0 to 8.0 inches; and, for the extra large size, the distance can range from 8.0 to 12.0 inches.

In the present invention, sensors $V_1$, $V_2$, $V_3$, and $V_4$ are positioned the same for all sizes of torsos. The center of $V_1$ is located on a point generally about 2.0 inches from the center of $V_2$ approximately on the 270 degree radial from the center of $V_2$ wherein the radial is measured with zero degrees measured from north at the top of $V_2$. The center of $V_4$ is located on a point generally 3.5 inches from the center of $V_2$ approximately on the 125 degree radial from the center of $V_2$. The center of $V_3$ is in line with $V_2$ and $V_4$ and is located on a point substantially between the center of $V_2$ and the center of $V_4$. The receptors $V_5$ and $V_6$ have four alternative positions each: all of the positions being disposed in the 90 degree radial from $V_4$. The centers of the $V_5$ positions are located approximately 1.75, 2.5, 3.5, and 5.0 inches from $V_4$ and the centers of the $V_6$ positions are located approximately 3.5, 5.0, 7.0, and 10.0 inches from $V_4$ whereby the centers of both $V_5$ and $V_6$ which are both located approximately 3.5 and 5.0 inches from $V_4$ share a common sensor in different sets of sensors.

The table below corresponds to the determined measurements for electrode placement which are all inherent in the present invention. It shows the preferred dimensional layout for $V_5$ and $V_6$ relative to $V_4$ for different sized torsos. Obviously, small variations in the lengths of the measurements are within the scope of the invention:

TABLE 1

| Size | $V_4$–$V_5$ | $V_5$–$V_6$ | $V_4$–$V_6$ |
|---|---|---|---|
| Small | 1.75" | 1.75" | 3.5" |
| Medium | 2.5" | 2.5" | 5.0" |
| Large | 3.5" | 3.5" | 7.0" |
| X-Large | 5.0" | 5.0" | 10.0" |

The distance between $V_1$ and $V_2$ is 2.0 inches, the distance between sternum centerline and $V_4$, along a horizontal line is 3.85 inches, and the distance between $V_2$ and $V_4$ along a vertical line is 2.0 inches, although this vertical distance could be up to 3.5 inches without considerably altering the effectiveness of the device. In addition, $V_3$ is located on a diagonal line between $V_2$ and $V_4$, and is equidistant from $V_2$ and $V_4$. These variations can be combined to create a universal mask by the use of four fixed position and two movable sensors to accommodate practically all adult sizes of torso. The mask of the present invention provides a plurality of sensors and sensor positions arranged in a predetermined dimensional array $V_1$–$V_6$ on the flexible sheet which inherently observes the dimensions dictated by Table I. In providing alternative locations of the sensors, the dimensional array on the flexible sheet becomes universal and the specific size configuration of the dimensional array or layout on the flexible sheet is determined in the same manner as for multiple sizes of masks to permit the production of an accurate electrocardial recording during ECG testing which can be reliably repeated.

The six sensors and alternate sensor positions are placed on the sheet in a geometric pattern approximating the standard precordial anatomical landmarks of any adult human being. The positioning of sensors $V_1$–$V_4$ is fixed and the same for all sizes of torsos and is shown in FIG. 1 as V1, V2, V3, and V4. The $V_5$ and $V_6$ positions each have four alternate positions including two independent sensor positions each: V5S and V5M for $V_5$, and V6L and V6XL for $V_6$. They also have two shared positions: V5L/V6S and V5XL/V6M. All of the $V_5$ and $V_6$ sensor positions lie along the same line with, and are spaced from, the $V_4$ sensor.

The $V_5$ and $V_6$ sensors are detachably secured to the sheet of the mask and are repositionable and can be resecured to any of the four separate sensor positions for each of $V_5$ and $V_6$, respectively. The mask is precut with perforations surrounding the $V_5$ and $V_6$ sensors and the adjacent portions of their integrated leads to allow detachment of the sensors from the array and repositioning of those sensors into cutouts or holes in the mask at the alternate $V_5$ and $V_6$ sensor positions. The precut portions of the mask are retained in position by the release liner and possibly small spaced-apart uncut connectors which interrupt the cut lines. A portion of the mask surrounding the leads for both of the sensors is also precut for a predetermined length thereof whereby the leads are detachable in variable length and are flexible to permit the repositioning of the $V_5$ and $V_6$ sensors.

The alternate sensor positions for $V_5$ or $V_6$ can be holes which are precut in the mask during manufacture or by die cut lines in the mask which form holes therein when the release liner is pulled off or removed from the mask taking those sensor positions of the mask surrounded by the cut lines with it. In the preferred embodiment of the invention, the detachable sensors and leads are outlined by cut lines which have connectors or the cut lines are formed by perforations whereby the sensors and leads remain attached to the mask until the liner is pulled off. The sensors and leads can be detached therefrom by the technician applying the mask to a patient by pulling on the tabs 41 which are attached to the movable sensors and provided for that purpose.

Alternatively, instead of forming holes in the mask, the alternate sensor positions in the mask can be made electrically transparent by perforating the mask at those positions whereby the electrically conductive gel transmits the electrical signals through the mask to the sensors attached thereto. The electrically transparent sensor positions are the equivalent of holes in the mask for the purposes of the invention.

The $V_5$ and $V_6$ sensors can be made slightly larger in size than the holes 39 provided in the mask for the alternate $V_5$ and $V_6$ positions so that the sensors overlap the edges of the holes when they are reattached to the mask and have been repositioned. Alternatively, the holes in the mask for the alternate $V_5$ and $V_6$ positions can be made larger than the movable sensors so that the sensors can be placed through the mask and attached directly to the patient's skin at those positions.

For very extra large patients, the applying technician may choose to place the two movable sensors even further from $V_4$ than the $V_5$ and $V_6$ sensor extra large alternate positions designated by the mask. This can be done by utilizing the embodiment of the invention shown in FIG. 1. The repositionable sensor can be placed under the mask at the selected extended positions, or by rolling the end of the mask back to expose the selected positions, or even by cutting off the end of the mask after the movable sensors have been detached therefrom for repositioning.

The design of the doubled back sensor leads of FIG. 1 allows the leads to be lengthened and extended further from V4 than the alternate sensor positions provided by the holes in the mask. In such cases, the mask is capable of accommodating essentially all sizes of the adult population.

The masks of FIGS. 1 and 2 show the perforation or cut lines for the sensors and the leads with pull tabs 41 on the sensors $V_5$ and $V_6$ to facilitate detaching the sensor and lead from the mask if it is necessary to move it. The particular design of FIG. 1 shows the detachable sensors arranged in the most probable location which is for medium sized persons. Most patients are accommodated by the medium sensor array, and therefore in most cases the sensors will be utilized in the medium positions. If the sensors are initially located in the medium sized torso positions, they will not need to be detached and repositioned.

Depending upon which $V_6$ position lies closest to the patient's midaxillary line, the $V_5$ and $V_6$ sensors and leads are, if necessary, partially detached from the mask and repositioned to the cutouts or holes which correspond to the patient's size determined by the location of the $V_6$ sensors on the patient's body. The $V_5$ and $V_6$ sensors will be repositioned to the corresponding sensor positions of the set of positions on the mask which includes the $V_6$ sensor lying closest to the patient's midaxillary line.

The sensor array shown by FIG. 2 is an alternative to FIG. 1 with the $V_5$ and $V_6$ sensors initially being disposed at the extra large torso size positions which is the simplest design and permits a simpler perforation cut on the $V_6$ sensor and its electrical lead because the edge of the mask forms one edge of the detachable lead for $V_6$, eliminating the need for an extra perforation cut in the mask during manufacture or in the cutting die.

When the mask is utilized for a small size torso, the repositionable $V_5$ sensor is secured at the first independent $V_5$ alternate sensor position V5S, disposed closest to the $V_4$ sensor position V4, and the repositionable $V_6$ sensor is secured at a first shared $V_5$ and $V_6$ alternate sensor position V5L/V6S which is also disposed closest to the $V_4$ position.

When the mask is utilized for a medium size torso, the repositionable $V_5$ sensor is secured at the second independent $V_5$ alternate sensor position V5M disposed furthest from the $V_4$ sensor position V4, and the repositionable $V_6$ sensor is secured at the second shared $V_5$ and $V_6$ alternate sensor position V5XL/V6M which is also disposed furthest from the $V_4$ position.

When the mask is utilized for a large size torso, the repositionable $V_5$ sensor is secured at the first shared $V_5$ and $V_6$ alternate sensor position V5L/V6S disposed closest to the $V_4$ sensor position V4, and the repositionable $V_6$ sensor is secured at the first independent $V_6$ alternate sensor position V6L which is also disposed closest to the $V_4$ position.

When the mask is utilized for an extra large size torso, the repositionable $V_5$ sensor is secured at the second shared $V_5$ and $V_6$ alternate sensor position V5XL/V6M disposed furthest from the $V_4$ sensor position V4, and the repositionable $V_6$ sensor is secured at the second independent $V_6$ alternate sensor position also disposed furthest from the $V_4$ position.

The first and second shared $V_5$ and $V_6$ sensor positions function either as the $V_5$ or $V_6$ positions depending upon the size of torso the sensor mask is being utilized on. When the mask is utilized for a small and large-size torsos, the first shared $V_5$–$V_6$ position functions as $V_6$ or $V_5$, respectively. When the mask is utilized for a medium and extra large-size torso, the second shared $V_5$–$V_6$ position functions as $V_6$ or $V_5$, respectively.

The sensor set selected for performing the ECG on a specific patient is recorded for the taking of subsequent ECGs on that patient to insure repeatability of sensor placement.

The present invention also contemplates a method for obtaining an electrocardiogram, and a method of sensor placement for performing twelve-lead electrocardiograms, by means of a universal ECG multiple sensor dermal precordial mask incorporating sensors $V_1$, $V_2$, $V_3$, $V_4$, $V_5$, and $V_6$. The mask is formed for fitting or accommodating different sizes of adult human bodies including extra large with repeatability and clinical efficacy of sensor $V_1$, $V_2$, $V_3$, $V_4$, $V_5$, and $V_6$ placement irrespective of the varying human body torso sizes and the different distances between the human body anatomical landmarks.

The method of sensor placement is comprised of several steps. A mask is provided which is formed for clinically efficacious placement of six precordial sensors on a patient's chest irrespective of torso size. The mask has a multiplicity of precordial sensor positions disposed in a specific geometrical pattern rather than in predetermined fixed arrays of individual sensor groups or an arbitrary individually located array of six precordial sensors. As few as six sensors can be utilized to serve as sensors for at least four different classes of human torso sizes.

In the preferred method of the invention, the mask is provided with an arrangement of at least ten precordial sensor positions which are arranged in or form at least four sets of sensor groups of six sensors each. Certain of the sensor positions serve the same function in each of the sets, and at least two of the sensors serve as a different designated sensor in different sets. In the preferred embodiment of the invention, the ten sensor positions are disposed in a specific geometric arrangement forming four sets of sensor groups which include four alternate sensor positions for each of the $V_5$ and $V_6$ sensor positions. The $V_1$–$V_4$ positions are fixed and are utilized for all four sizes of bodies.

Two sensors and the electrical leads therefor are releasably secured to the mask for subsequent repositioning onto two of the four respective alternative $V_5$ and $V_6$ sensor positions. In all four groups, two sensor positions serve for either $V_5$ or $V_6$ in the four different sensor sets whereby four sets of six sensor positions each are provided by the ten sensor positions to locate six of the sensors proximate the standard precordial anatomical landmarks of four different classes of sizes of human torsos.

The mask is provided with indicia for positioning it on a patient's sternum centerline and the fourth intercostal space and for determining which sensor positions correspond to the four sensor sets. The latter is done by determining which of the four $V_6$ positions lies on or closest to the patient's midaxillary line.

The mask is placed on a patient's chest and the first positioning indicia on the mask are aligned with the corresponding anatomical positions on the patient's chest so that $V_1$ and $V_2$ are disposed approximately on opposite sides of the patient's sternum. Two of the six sensor positions for $V_5$ and $V_6$ are then selected for performing an ECG depending upon the torso size of the patient by ascertaining from the mask's second indicia which of the four $V_6$ sensor positions lies on or closest to the patient's midaxillary line. When the $V_6$ sensor position lying closest to the patient's midaxillary line has been determined and the patient's size has been established from the indicia on the mask as V6S, V6M, V6L, V6XL, then the $V_6$ sensor is repositioned, if necessary, to the determined $V_6$ sensor position if it is not already disposed at that position. In the same manner, the $V_5$ sensor corresponding to the determined $V_6$ sensor is also repositioned, if necessary, to the corresponding $V_5$ sensor position if it is not already disposed at that position.

Sensor leads from ECG test apparatus are connected to the six sensors which include the identified $V_6$ position and the corresponding $V_5$ position, and electrocardiographic information is obtained from those sensors.

Thus, in summary, both an apparatus and methods for torso sizing and sensor placement for performing twelve-lead electrocardiograms are provided, and the stated objects of the present invention are achieved. A single mask design, having only six sensors instead of three or four different sizes of masks, as taught by the prior art, provides a universal size which can be utilized to obtain the benefits of simplified high volume production in order to lower the cost to the user and reduce the time previously needed to establish the size of a patient. The preferred embodiment of the present invention solves the problems associated with high variability of individual sensor placement which may produce inaccurate ECGs, and thus an incorrect diagnosis, and which problems prevent valid and reliable serial comparisons between repeat ECGs on the same patient.

The present invention eliminates the logistics of maintaining different size sensor masks. This includes the stock in the central supply of a hospital, stock rooms of wards and clinics, and individual ECG carts. A related benefit is that stock would be depleted evenly thereby eliminating the possibility that some stock, e.g., a less often used size in a four-size system, might not be used prior to reaching an expiration date. The one size design of the present invention eliminates the steps required to determine a patient's torso size and fits essentially all of the adult torso population including extra large. Any possibility of error when sizing a patient is eliminated.

The method of the present invention is one in which there is less waste since essentially all adult patients are accommodated by the one device. With more than one device size, there is the possibility that a wrong size would be applied to a patient and would need to be removed and discarded prior to applying the correct size device. This trial and error situation would also increase the time spent performing an ECG on one patient. This is eliminated by the present invention.

It is also an object of the present invention to permit the taking of four different ECGs simultaneously with the same device. Because the device contains four precordial sensor patterns, it is possible to take four different ECGs by connecting to each pattern in turn by simply reapplying the single six-conductor connectors serially to the four terminal sets. This may provide additional diagnostic information beyond what is now obtained from a conventional ECG using six precordial sensor locations.

Thus, it will be apparent from the foregoing description of the invention in its preferred form that it will fulfill all the objects and advantages attributable thereto. While it is illustrated and described in considerable detail herein, the invention is not to be limited to such details as have been set forth except as may be necessitated by the appended claims.

What is claimed is:

1. A method for obtaining electrocardiograms by means of a universal ECG multiple sensor dermal precordial mask incorporating sensors $V_1$, $V_2$, $V_3$, $V_4$, $V_5$, and $V_6$ for fitting different sizes of human bodies including extra large, said method comprising the steps of providing a mask having at least ten precordial sensor positions disposed in a specific geometric arrangement and forming at least four sets of sensor groups including four alternate sensor positions for each of said $V_5$ and $V_6$ sensors, said $V_1$–$V_4$ sensor positions being utilized for all sizes of bodies and said $V_5$ and $V_6$ positions, each having two independent sensor positions and sharing two positions corresponding to said four sensor sets, said $V_5$ and $V_6$ sensors being releasably secured to said mask as detachable sensors with detachable variable length and flexible leads formed integral thereto whereby said $V_5$ and $V_6$ sensors are repositionable to each of said respective $V_5$ and $V_6$ alternate sensor positions, and said mask including indicia for determining which alternate $V_5$ and $V_6$ sensor positions correspond to said four sensor sets, aligning said mask on a patient's chest so that said $V_1$ and $V_2$ are disposed approximately on opposite sides of the patient's sternum, ascertaining from said indicia which of said four $V_6$ sensor positions lies on or is closest to the patient's midaxillary line, detaching if necessary said releasably secured $V_5$ and $V_6$ sensors and then repositioning them onto the corresponding sensor positions of said set of positions on said mask which includes said $V_6$ sensor position lying closest to the patient's midaxillary line, and obtaining electrocardiographic information from said fixed position $V_1$–$V_4$ sensors and said movable $V_5$ and $V_6$ sensors.

2. The method of claim 1 wherein said repositionable sensors and leads are initially disposed at the sensor positions for one of the said four sets of sensor positions.

3. The method of claim 1 wherein said alternate $V_5$ and $V_6$ sensor positions are disposed along a horizontal line.

4. The method of claim 1 wherein said alternate $V_5$ and $V_6$ sensor positions on said mask are comprised of holes therein through which the movable sensor leads can be secured to the patient's skin.

5. A method of sensor placement for performing twelve lead electrocardiograms by means of a universal ECG multiple sensor dermal chest mask formed for fitting or accommodating different sizes of adult human bodies including extra large with repeatability and clinical efficacy of sensors $V_1$, $V_2$, $V_3$, $V_4$, $V_5$, and $V_6$ placement irrespective of the varying human body torso sizes and the different distances between the human body anatomical landmarks, said method of sensor placement comprising the steps of providing a mask having at least ten precordial sensor positions disposed in a specific geometric arrangement rather than in predetermined fixed arrays of individual sensor groups or an arbitrary individually located array of six precordial sensors needed for a resting ECG, said arrangement of ten sensor positions forming four sets of sensor groups including four alternative sensor positions for each of said $V_5$ and $V_6$ in which two sensor positions serve for either $V_5$ or $V_6$ in four different sensor sets whereby four sets of six sensor positions each are provided by said ten sensor positions to position six of said sensors proximate to the anatomical landmarks of four different classes of sizes of human torsos, said mask including first indicia for positioning said mask on a patient's sternum centerline and the fourth intercostal space and second indicia for determining which sensor positions correspond to said four sensor sets, providing six sensors for said ten sensor positions wherein four of said sensors and the leads therefor are positioned at said $V_1$–$V_4$ sensor positions and two sensors and leads therefor are releasably secured to said mask for subsequent repositioning onto two of said four respective alternative $V_5$ and $V_6$ sensor positions, placing said mask on a patient's chest and aligning said first positioning indicia on said mask with said patient's corresponding anatomy, ascertaining from said second indicia which of the four $V_6$ sensor positions lies on or closest to the patient's midaxillary line, repositioning said two sensors and the leads therefor if necessary onto the corresponding $V_5$ and $V_6$ sensor positions in said set of sensor positions which includes said $V_6$ sensor position lying closest to the patient's midaxillary line, and connecting ECG test apparatus to said sensor lead wires from said six sensors.

6. A universal ECG multiple sensor dermal precordial mask for fitting different sizes of human bodies including extra large for obtaining electrocardiographic information using sensors $V_1$, $V_2$, $V_3$, $V_4$, $V_5$, and $V_6$, said mask comprising a sheet of non-conductive material incorporating at least six sensors and ten sensor positions disposed in a specific geometric arrangement with said $V_1$–$V_4$ sensors being utilized for all sizes of bodies, said ten sensor positions including four alternate positions for each $V_5$ and $V_6$ positions, said $V_5$ and $V_6$ sensors having first and second independent sensor positions each and first and second shared positions and being detachably secured to said sheet and repositionable and resecurable to any of the four separate sensor positions for each of $V_5$ and $V_6$.

7. A universal ECG multiple sensor dermal precordial mask for fitting different sizes of human bodies including extra large for obtaining electrocardiographic information using sensors $V_1$, $V_2$, $V_3$, $V_4$, $V_5$, and $V_6$, said mask comprising a flexible sheet of non-conductive material incorporating at least ten sensor positions disposed in a specific geometric arrangement forming four sets of sensor groups including four alternate positions for each $V_5$ and $V_6$ position disposed along a horizontal line and including first and second independent sensor positions each and first and second shared positions, said $V_1$–$V_4$ positions including fixed sensors utilized for all sizes of bodies, and said $V_5$ and $V_6$ sensors being detachably secured to said sheet and repositionable and attachable to a patient's skin through holes in said mask and at any of the four separate sensor positions for each of $V_5$ and $V_6$.

8. A mask as set forth in claim 7, wherein when said mask is utilized for a small size torso, said repositionable $V_5$ sensor is secured at said first independent $V_5$ sensor position disposed closest to said $V_4$ position and said repositionable $V_6$ sensor is secured at said first shared $V_5$ and $V_6$ position which is also disposed closest to said $V_4$ position, when said mask is utilized for a medium size torso, said repositionable $V_5$ sensor is secured at said second independent $V_5$ sensor position, disposed furthest from said $V_4$ position, and said repositionable $V_6$ sensor is secured at said second shared $V_5$ and $V_6$ position which is also disposed furthest from said $V_4$ position, when said mask is utilized for a large size torso, said repositionable $V_5$ sensor is secured at said first shared $V_5$ and $V_6$ sensor position and said repositionable $V_6$ sensor is secured at first independent $V_6$ position disposed closest to said $V_4$ sensor position, and when said mask is utilized for an extra large size torso, said repositionable $V_5$ sensor is secured at said second shared $V_5$ and $V_6$ sensor position and said repositionable $V_6$ sensor is secured at said second independent $V_6$ sensor position which is disposed furthest from said $V_4$ position.

9. The mask as set forth in claim 7 wherein said $V_1$ and $V_2$ sensor positions are disposed equidistant from the patient's sternum and on the fourth intercostal space, the center of said $V_1$ position is located approximately 2.0 inches from the center of said $V_2$ position on the 270 degree radial therefrom, the center of said $V_4$ position is located approximately 3.5 inches from the center of said $V_2$ position on the 125 degree radial therefrom, the center of said $V_3$ position is disposed on a line and equidistant between said $V_2$ and said $V_4$ positions, and said $V_5$ and $V_6$ positions have four alternative positions each, all of said positions being disposed on a 90 degree radial from said $V_4$ position, the centers of said $V_5$ positions being located 1.75, 2.5, 3.5, and 5.0 inches therefrom and the centers of said $V_6$ positions being located 3.5, 5.0, 7.0, and 10.0 inches therefrom whereby the centers of said $V_5$ and $V_6$ positions which are both located 3.5 and 5.0 inches from said $V_4$ position share a common position in the different sets of sensors.

10. A disposable universal ECG multiple sensor dermal chest mask for fitting or accommodating different sizes of adult human bodies including extra large for performing twelve lead electrocardiograms with repeatability and clinical efficacy of sensor $V_1$, $V_2$, $V_3$, $V_4$, $V_5$, and $V_6$ placement irrespective of the varying human body torso sizes and the different distances between the human body anatomical landmarks, said mask comprising a flexible sheet of non-conductive material having ten sensor positions disposed in a single pattern rather than in predetermined fixed arrays of individual sensor groups or an arbitrary individually located array of six precordial sensors which are needed for a resting twelve-lead ECG, said sensor positions disposed on said sheet in a specific geometric arrangement, said $V_1$–$V_4$ sensor positions including sensors which are utilized for all sizes of bodies, and said $V_5$ and $V_6$ sensor positions each having four alternate positions including first and second independent sensor positions each and first and second shared positions, said $V_5$ and $V_6$ sensors being detachably secured to said sheet and repositionable and attachable to a patient's skin through holes in said mask at any of the four separate sensor positions for each of $V_5$ and $V_6$, said $V_1$ and $V_2$ sensor positions being disposed to lie on opposite sides of a patient's sternum equidistant therefrom and on the fourth intercostal space, the center of said $V_1$ position being located approximately 2.0 inches from the center of said $V_2$ position on the 270 degree radial therefrom, the center of said $V_4$ position being located approximately 3.5 inches from the center of said $V_2$ position on the 125 degree radial therefrom, the center of said $V_3$ position being disposed on a line and equidistant between said $V_2$ and said $V_4$ positions, and said $V_5$ and $V_6$ sensors having four alternative positions each, all of said positions being disposed on a 90 degree radial from said $V_4$ position, the centers of said $V_5$ positions being located 1.75, 2.5, 3.5, and 5.0 inches therefrom and the centers of said $V_6$ positions being located 3.5, 5.0, 7.0, and 10.0 inches therefrom whereby the centers of said $V_5$ and $V_6$ positions which are both located 3.5 and 5.0 inches from said $V_4$ position share a common position in the different sets of sensors, whereby when said mask is utilized for a small size torso, said repositionable $V_5$ sensor is secured at said first independent $V_5$ sensor position disposed closest to said $V_4$ sensor position and said repositionable $V_6$ sensor is secured at said first shared $V_5$ and $V_6$ sensor position which is also disposed closest to said $V_4$ position, when said mask is utilized for a medium size torso, said repositionable $V_5$ sensor is secured at said second independent $V_5$ sensor position disposed furthest from said $V_4$ sensor position and said repositionable $V_6$ sensor is secured at said second shared $V_5$ and $V_6$ sensor position which is also disposed furthest from said $V_4$ position, when said mask is utilized for a large size torso, said repositionable $V_5$ sensor is secured at said first shared $V_5$ and $V_6$ sensor position and said repositionable $V_6$ sensor is secured at said first independent $V_6$ sensor position which is disposed closest to said $V_4$ sensor position, and when said mask is utilized for an extra large size torso, said repositionable $V_5$ sensor is secured at said second shared $V_5$ and $V_6$ sensor position and said repositionable $V_6$ sensor is secured at said second independent $V_6$ sensor position which is disposed furthest from said $V_4$ sensor position.

* * * * *